United States Patent [19]

Svedman et al.

[11] Patent Number: 5,176,663
[45] Date of Patent: Jan. 5, 1993

[54] DRESSING HAVING PAD WITH COMPRESSILITY LIMITING ELEMENTS

[75] Inventors: Pal Svedman, Ostanvag 85 B, S-216 19 Malmö ; Lars-Erik Kileby, Mölnlycke, both of Sweden

[73] Assignee: Pal Svedman, Malmo, Sweden

[21] Appl. No.: 759,139

[22] Filed: Sep. 11, 1991

Related U.S. Application Data

[63] Continuation of Ser. No. 476,479, Jul. 20, 1990.

[30] Foreign Application Priority Data

Dec. 2, 1987 [SE] Sweden ............................. 8704821-1
Dec. 2, 1988 [SE] Sweden ................ PCT/SE88/00660

[51] Int. Cl.⁵ ............................................. A61F 13/00
[52] U.S. Cl. ...................... 604/305; 602/47; 602/59; 128/888; 604/378
[58] Field of Search ................ 128/155, 888, 887, 889, 128/894; 604/378, 383, 305; 602/47, 59

[56] References Cited

U.S. PATENT DOCUMENTS

| | | | |
|---|---|---|---|
| 2,404,758 | 7/1946 | Teague et al. | 128/155 |
| 2,896,618 | 7/1959 | Schaefer | |
| 3,122,142 | 2/1964 | Crowe, Jr. | 604/383 |
| 3,304,938 | 2/1967 | Perkins, Jr. | 128/888 |
| 3,498,296 | 3/1970 | Gallagher | 604/378 |
| 3,561,441 | 2/1971 | Lembardi | |
| 3,929,135 | 12/1975 | Thompson | |
| 3,989,867 | 11/1976 | Sisson | 428/132 |
| 4,643,727 | 2/1987 | Rosenbaum | |
| 4,935,087 | 6/1990 | Gilman | 128/155 |

FOREIGN PATENT DOCUMENTS

| | | | |
|---|---|---|---|
| 0040084 | 11/1981 | European Pat. Off. | |
| 2520856 | 11/1976 | Fed. Rep. of Germany | 128/155 |
| 3515541 | 12/1985 | Fed. Rep. of Germany | 128/155 |
| 2218078 | 9/1974 | France | |
| 8008971 | 7/1985 | Sweden | |
| 1571922 | 7/1980 | United Kingdom | |

*Primary Examiner*—Paul Prebilic
*Attorney, Agent, or Firm*—Cushman, Darby & Cushman

[57] ABSTRACT

A dressing with a pad to be applied to a wound and consisting of a flexible, capillary-active material and stiffening elements. The stiffening elements extend at right angles to the flat side of the pad to be applied to the wound and are arranged to stabilize the volume of the pad such that it can absorb a predeterminable amount of fluid, and to counteract and distribute forces acting on the pad. To form an occlusive dressing, the pad can be enclosed in a cover of vapour-permeable, plastic film having a perforated portion on the flat side of the pad facing the wound.

14 Claims, 1 Drawing Sheet

DRESSING HAVING PAD WITH COMPRESSIBILITY LIMITING ELEMENTS

This is a continuation of U.S. application Ser. No. 07/476,479, filed on Jul. 20, 1990, which was abandoned.

BACKGROUND OF THE DISCLOSURE

The present invention relates to a dressing with a pad made of a flexible, capillary-active material, intended to be applied to a wound.

Dressings are used for treating e.g. surgical wounds, open wounds and portions of the skin subjected to pressure. Dressings ready for use are adapted to these applications and fulfil the following functions to a varying degree.

1. PROTECTION AND IMMOBILISATION

By avoiding pressure, shocks and motion in the tissue area, it is possible to prevent or reduce tissue injury. The less the tissue injury is, the more efficient becomes infection control and healing. Pain is relieved.

2. ISOLATION

If the wound is clean, infection is prevented. If the wound is already infected, the infection is prevented from spreading to surrounding areas. Unnecessary direct contact with the patient's body fluids should be avoided, which means that leakage of pus and blood from the dressing should be prevented as far as possible. The demand for isolation has become still more justified with the advent of new sources of infection, such as AIDS.

3. PREVENTION OF EVAPORATION AND DEHYDRATION

This is of importance in open wounds. Healing here takes place e.g. by ingrowth of the cells of the skin from the edge portions of the wound. These cells are especially sensitive to an unfavourable environment, and dehydration means that healing will be considerably delayed.

4. ACTIVE INFLUENCE

This can be achieved by adding chemical substances, such as infection control agents or healing substances, or by removing bacteria and pus from the surface of the wound and the dressing.

For a better idea of the prior art, a brief account of conventional ready-for-use dressings and their major drawbacks will now be given.

1. DRESSINGS FOR SURGICAL WOUNDS

A dressing of this type includes a pad to be applied to a wound and disposed centrally on a thin backing layer of gauze or nonwoven material. Around the pad, the backing layer is provided with adhesive for fixing the dressing to the skin surrounding the wound. The pad typically is constituted by a piece of absorbent felt. Superposed absorbent layers of felt having different density and rigidity are sometimes used. The backing layer is air- and liquid-permeable. In use, blood or pus is absorbed by the pad. If a dressing partially saturated with liquid is subjected to pressure, e.g. when the patient is lying on the dressing or parts of the bandage located outside are compressed, there is a reduction of the volume of the pad which is capable of retaining liquid. The backing layer is soaked and the isolating air seal against the environment is broken, which means both risk of infection and practical inconveniences. An unplanned change of dressings may be necessitated. Thus, this type of dressing cannot be considered volumetrically stable in the sense that a given volume of blood or pus can always be retained in the dressing.

2. DRESSINGS FOR OPEN WOUNDS

Occlusive dressings used are in the form of a plastic film or adhesive plate. The dressing materials are either completely occlusive or vapourpermeable to a varying degree. They are not permeable to water. Evaporation of clinical importance is prevented, like dehydration. The occlusive film consists of a piece of adhesive elastic polymer film applied to the wound and the surrounding skin. The adhesive surface adheres to the skin whereas not to the wound, thus forming a watertight wound pocket which may contain wound exudate or pus. A considerable drawback is that such a pocket has no volumetric stability. If the liquid retained is subjected to pressure, the above-mentioned consequences are experienced. Further, the film affords no protection against pressure, shocks or motion. Active influence is not possible. The occlusion plate is made of a thin foam material having a coating of polymer film and provided on one side with a slightly thicker layer of adhesive. The adhesive forms together with the pus a low-viscosity gel. This plate suffers from the same drawbacks as the occlusive film. Since there is no volumetrically stable space, undesired leakage may take place under the conditions stated above. As opposed to the film, the plate provides a certain protection and immobilisation. Active influence on the wound is not possible. The flush dressing is a special type of occlusive dressing which also allows active influence on the wound. It consists of a wound pad which is in the form of a piece of felt covered with polymer film. One or more central perforations are facing the wound, otherwise the film is watertight. The surface of the film surrounding the perforations is adhesive and allows occlusive application to the skin surrounding the wound. The dressing has two connections which can be used simultaneously for supplying treatment liquid and for draining pus or wound exudate. The liquid supplied is distributed in the open capillary-active pore system of the pad. Drainage is effected by applying a negative pressure which is also distributed in the pore system. A major drawback here is that the dressing is not volumetrically stable and so, leakage may occur (see above). Further, functional trouble may arise if the capillary-active pore system is occluded by compression, which may also be caused by a negative pressure in the dressing.

3. PROTECTIVE DRESSING

Protracted pressure may cause injury and give rise to wounds also in normal skin. The protective dressing relieves a portion of the skin subjected to pressure and is used in the prophylaxis of pressure-induced wounds, primarily in bedridden, immobilised patients. The occlusion plate is now being used for this purpose. Since the plate is thin and has no reinforcement, only insufficient relief is obtained.

SUMMARY OF THE INVENTION

The object of the present invention is to overcome the drawbacks inherent in prior art dressings, by providing a dressing which can be used as an ordinary dressing and as occlusive dressing, flush dressing, dressing for surgical wounds as well as protective dressing, and which by dimensional stabilisation can absorb a predetermined amount of fluid from a wound and efficiently protects the wound from stresses. This object is achieved in that the dressing has elements of a given rigidity and length orthogonally to the flat side of the pad to be applied to the wound, these elements being adapted both to stabilise the volume of the pad so as to give it a predeterminable liquidabsorbing volume, and to counteract and distribute the forces directed against the pad.

BRIEF DESCRIPTION OF THE DRAWING

The invention will now be described in more detail hereinbelow with reference to the accompanying drawing schematically showing an embodiment of an occlusive dressing.

In the Drawing.

DETAILED DESCRIPTION

Figure 1:
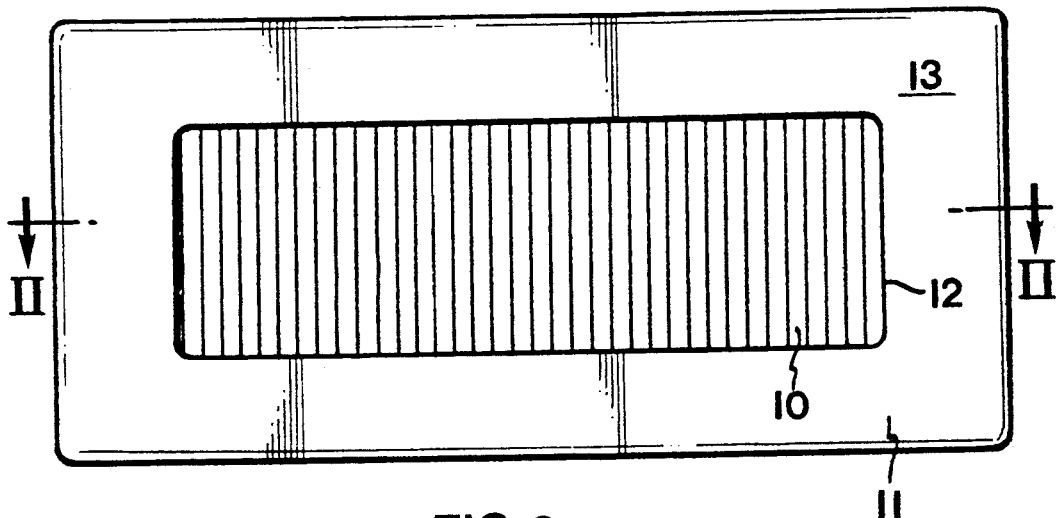
FIG. 1 is a bottom plan view of a dressing according to the invention.

The dressing according to the invention comprises a pad 10 intended to be applied to a wound and made of capillary-active material, i.e. a material which is able to absorb fluids from a wound when the pad is applied to it. This material may be woven or nonwoven or consist of a foam material having open cells and being of a nature to minimise adhesion to the wound. The capillary-active material 10 is enclosed in a cover of plastic sheeting or film 11 which covers the top side of the pad and extends as a single piece therefrom around the edges of the pad so as also to cover the bottom side of the pad 10. In the part of the sheeting which covers the bottom side of the pad, there is provided a perforated portion 12 the boundary edges of which are spaced from the edges of the pad so as to form a non-perforated frame of sheeting 13 coated with a suitable adhesive, such as acrylic glue or cellulose synthetic rubber glue adhering to and absorbing moisture from the skin. The film or sheeting 11 is liquid-tight, but preferably vapour-permeable and may be translucent. Instead of a film or sheeting 11 of plastic material, it is possible to use a film or sheeting of other materials, such as natural or synthetic rubber. The essential thing is that the film or sheeting be liquid-tight and has the desired airtightness. The pad 10 preferably tapers towards its edges, as indicated at 20 in FIG. 2.

Figure 2:
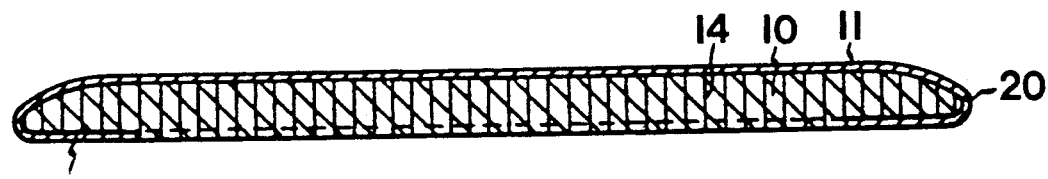
FIG. 2 is a section taken along the line II—II in FIG. 1.

The pad 10 has stiffening elements which extend between the opposite flat sides of the pad and which may be of different types. In the embodiment shown in FIG. 2, the stiffening elements comprise walls 14 extending between the opposite flat sides of the pad. In FIG. 2, the walls 14 extend between the opposite long sides of the dressing, but they may also extend between the short sides or between both the short sides and the long sides, so as to form a grating. The walls 14 can be obtained in different ways. Thus, for example, the pad may first be manufactured with the walls 14, after which the space between the walls is filled with capillary-active material. It is also possible to manufacture the pad 10 in one working operation by also making the walls 14 from the capillary-active material, however giving them in a suitable manner during the manufacturing process a higher density than the intermediate material so that they become more rigid than this latter material. If the capillary-active material is made of thermoplastic, it is possible, by means suitably shaped, to provide e.g. tubular or hourglass-shaped formations oriented with their longitudinal direction at right angles to the flat sides of the pad 10 and having a wall of increased rigidity, counteracting and distributing the forces exerted on the outer side of the dressing. The stiffening walls 14 may also form an oblique angle or a latticework with the perforated portion 12.

Figure 4:
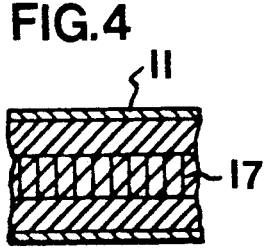
FIGS. 4, 5 and 6 illustrate specific embodiments of the dressing.

According to FIG. 4, the layer of stiffening elements need not extend between the flat sides of the pad, but may be provided as a thinner layer of elements 17 which, as shown in the figure, may be disposed centrally in the pad and have capillary-active material between it and the flat sides of the pad, but which may also be located adjacent e.g. the outwardly facing side thereof, with capillary-active material filling the space between the layer of stiffening elements and the inwardly facing side of the pad.

Instead of the above-mentioned formations, the pad may be provided with cushions 18 extending between the opposite flat side surfaces of the pad. These cushions 18 may be made from a sheeting material and be filled with air or elastic material.

Figure 5:
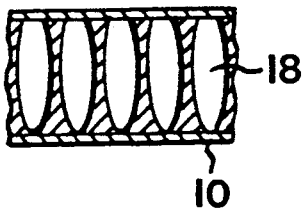
Figure 6:
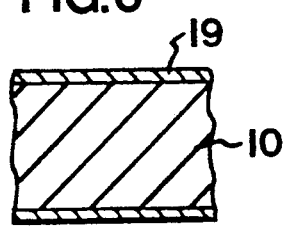

The stiffening elements need not necessarily be provided in the pad, but may instead be connected to the sheeting, which may be achieved e.g. by embossing the sheeting in a suitable manner. For joining the sheeting 11 to the pad, the elements are pressed down into the pad, yielding an arrangement which resembles that shown in FIG. 5.

In certain applications, it may be suitable to use a thicker and optionally also reinforced sheeting 19 on one or both of the opposite flat sides of the pad. Such a stronger sheeting is suitably used when the dressing may be expected to be subjected to substantial stress. Instead of a sheeting, it is possible to use a foam material with closed cells.

Figure 3:
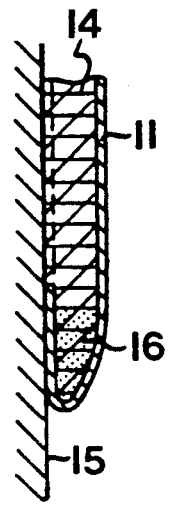
FIG. 3 shows an edge portion of the dressing in vertical position.

Although the volume of fluid which can thus be taken up by the pad is limited by the existing volume of air, the capillary-active component makes it possible for the pad to take up even more fluid. When, in the use of the dressing, fluid is taken up in the pad, an excess pressure is produced therein, which is however equalized if the sheeting is vapour-permeable. Due to the arrangement of stiffening means, it is possible to accurately determine the amount of fluid that can be absorbed, and the dressing is chosen according to the nature of the wound. Thus, if considerable amounts of fluid are expected, a dressing with an extra thick pad is chosen. As pointed out above, the stiffening elements 14, 17 and 18 also ensure that the wound is protected against stress, such as shocks, to which the dressing may unintentionally be subjected. A further advantage of the dressing is that the absorbed fluid is collected in the pocket 16 formed by folding the sheeting around the edges of the pad, as shown in FIG. 3. Thus, the fluid will not tend to leak out between the sheeting and the underlying skin 15 if the dressing is oriented as shown in FIG. 3.

To protect the wound and distribute the forces exerted on the dressing, the stiffening elements may be joined to each other in their ends adjacent the wound, by means of intermediate arms or formations which between them and the ends of the elements define liquid-permeable (capillary) openings.

Figure 7:
FIG. 7 is a fragmentary longitudinal sectional view of a modified form of the dressing, in which an inlet and an outlet are shown for flushing the wound through the dressing.

The dressing according to the invention is useful for both open wounds and surgical wounds. The pad may be impregnated with healing agents, and the dressing may also be provided, as shown in FIG. 7, with inlets 30 and/or outlets 32, preferably both, for circulation of treatment liquid (flush dressings), as described in Swedish Patent 8008971-9. Moreover, the dressing can be used as a protective dressing of the design can be used as a protective dressing of the design shown in FIG. 1, but in such a case the perforated portion preferably consists of a plurality of micropores in the area which in FIG. 1 is occupied by the single, large hole in the sheeting 11.

The pad may have hydrophobic or hydrophilic properties, optionally alternating in different layers. The surface may be heparinised or provided with a bactericide.

We claim:

1. A dressing for a wound, comprising:
    a pad of flexible, capillary-active material having a flat bottom side adapted to be presented facewise towards a wound, a top side, and an outer perimetrical edge extending between said top and bottom sides;
    means for limiting thicknesswise compressibility of said pad, said compressibility-limiting means including a plurality of elements having a greater resistance to compression thicknesswise of said pad than does said pad of capillary-active material said elements extending over a major portion of the thickness of said dressing and being arranged generally orthogonally to the plane of said bottom side; said elements further being widely distributed within the perimeter of said pad, so that said compressibility-limiting means, in use, provide said pad, with a stable volume and with a means for distributing and limiting effects of compressive forces applied on said top side of said pad;
    said compressibility-limiting means having two opposite ends which are respectively flush with said bottom side and said top side of said pad.

2. The dressing of claim 1, wherein:
    said elements of said compressibility-limiting means are arranged in a grid.

3. The dressing of claim 1, further comprising:
    said pad being enclosed by a covering of liquid-impermeable sheeting; opening means being defined through said sheeting only in a central portion of said bottom side of said pad, said central portion thereby being surrounded on said bottom side of said pad by an imperforate frame of said liquid-impermeable sheeting, said frame having an external surface;
    means providing a coating of adhesive on said external surface of said frame, for adhering said dressing to a patient over a wound.

4. The dressing of claim 3, wherein:
    said opening means is constituted by one large hole.

5. The dressing of claim 3, wherein:
    said opening means is constituted by a plurality of perforations.

6. The dressing of claim 1, wherein:
    said pad tapers in thickness from centrally thereof towards said edge all around the outer perimeter thereof.

7. The dressing of claim 3, further comprising:
    said pad being enclosed by a covering of liquid-impermeable sheeting; opening means being defined through said sheeting in a central portion of said bottom side of said pad, said central portion thereby being surrounded on said bottom side of said pad by an imperforate frame of said liquid-impermeable sheeting, said frame having an external surface;
    means providing a coating of adhesive on said external surface of said frame, for adhering said dressing to a patient over a wound; and
    means defining a plurality of perforations through said sheeting upon at least one of the top side and edge of said pad.

8. The dressing of claim 3, further comprising:
    said pad being enclosed by a covering of liquid-impermeable sheeting; opening means being defined through said sheeting in a central portion of said bottom side of said pad, said central portion thereby being surrounded on said bottom side of said pad by an imperforate frame of said liquid-impermeable sheeting, said frame having an external surface;
    means providing a coating of adhesive on said external surface of said frame, for adhering said dressing to a patient over a wound; and
    said sheeting, upon at least one of said sides of said pad, is made of closed cell foam.

9. The dressing of claim 20, further comprising:
    said pad being enclosed by a covering of plastic sheeting; said sheeting, upon at least one of said sides of said pad, being made of closed cell foam;
    opening means being defined through said sheeting in a central portion of said bottom side of said pad.

10. The dressing of claim 9, wherein:
    said elements of said compressibility-limiting means are arranged in a grid.

11. The dressing of claim 9, wherein:
    said opening means is constituted by one large hole.

12. The dressing of claim 9, wherein:
    said opening means is constituted by a plurality of perforations.

13. The dressing of claim 9, wherein:
    said pad tapers in thickness from centrally thereof towards said edge all around the outer perimeter thereof.

14. The dressing of claim 3, further including: means providing an inlet to and an outlet through said covering on said top side of said pad, said inlet and outlet being arranged for flushing said wound.

* * * * *